US 6,773,814 B2

(12) United States Patent
Schumacher et al.

(10) Patent No.: US 6,773,814 B2
(45) Date of Patent: Aug. 10, 2004

(54) METAL OXIDE PARTICLES COATED WITH SILICON DIOXIDE

(75) Inventors: Kai Schumacher, Hofheim (DE);
Helmut Mangold, Rodenbach (DE);
Steffen Hasenzahl, Hanau (DE);
Harald Alff, Kahl (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/212,741

(22) Filed: Aug. 7, 2002

(65) Prior Publication Data

US 2003/0104198 A1 Jun. 5, 2003

(30) Foreign Application Priority Data

Aug. 8, 2001 (EP) .......................................... 01119108

(51) Int. Cl.⁷ .............................. B23B 5/16; B05D 3/00
(52) U.S. Cl. ........................ 428/404; 51/308; 51/309; 106/3; 106/286.8; 106/287.34; 424/401; 424/490; 424/688; 424/724; 427/215; 427/219; 427/372.2; 427/397.7; 427/444
(58) Field of Search ................................ 428/403, 404; 51/308, 309; 106/3, 286.8, 287.34; 424/401, 490, 688, 724; 427/215, 219, 372.2, 397.7, 444

(56) References Cited

U.S. PATENT DOCUMENTS

| 4,801,445 | A | * | 1/1989 | Fukui et al. ................... 424/69 |
| 4,874,594 | A | * | 10/1989 | Chevallier ................ 220/254.1 |
| 6,086,668 | A | | 7/2000 | Farneth et al. |
| 6,165,510 | A | * | 12/2000 | Baines et al. ................ 424/489 |
| 6,193,795 | B1 | * | 2/2001 | Nargiello et al. ........... 106/484 |
| 6,235,270 | B1 | | 5/2001 | Ishii et al. |
| 6,534,044 | B1 | * | 3/2003 | Wada et al. ................... 424/59 |

FOREIGN PATENT DOCUMENTS

| EP | 0 908 494 A2 | 4/1999 |
| EP | 0 988 853 A1 | 3/2000 |
| EP | 1 078 957 A1 | 2/2001 |
| JP | 10 297914 | 11/1998 |

* cited by examiner

Primary Examiner—H. Thile
(74) Attorney, Agent, or Firm—Oblon, Spivak, McClelland, Maier & Neustadt, P.C.

(57) ABSTRACT

Metal oxide particles having a metal oxide core and a silicon dioxide coating have a low structure. The particle are produced by a base dissolved in water being added under agitation to a dispersion comprising a metal oxide, at least one compound of the type $X_n Si(OR)_{4-n}$, and water, the reaction product being separated out, optionally washed with water and dried. The metal oxide particles coated with silicon dioxide may be used in sun screening agents and in chemical-mechanical-polishing (CMP) applications.

20 Claims, 3 Drawing Sheets

1 μm

1 μm

METAL OXIDE PARTICLES COATED WITH SILICON DIOXIDE

BACKGROUND OF THE INVENTION

1. Field of the Invention

The invention relates to metal oxide particles coated with silicon dioxide, a process for their production, and their use.

2. Description of the Background

Metal oxides, such as titanium dioxide or zinc oxide are widely used in sun screening agents. Their action is substantially based on the reflection, scattering and absorption of harmful UV radiation and is substantially dependent upon the primary particle size of the metal oxides.

The drawback of metal oxides such as titanium dioxide or zinc oxide is their photocatalytic activity through which reactions are triggered which may lead to changes to components of a sun screening agent.

Attempts are being made to reduce the photocatalytic activity of these metal oxides without reducing the UV-screening properties by, for example, surrounding them with a coating.

EP-A-0 988 853 describes metal oxide particles coated with silicon dioxide, plus their production and use as a component in sun screening agents. Here, the drawback is that these coated metal oxide particles have low surface functionality and a high degree of particle coalescence. On the one hand, this hampers the incorporation of the particles in a cosmetic formulation and, on the other hand, it restricts their resistance with regard to sedimentation. Another drawback is the fact that during the production of these particles, in addition to water, an organic solvent is essential to enable a coating to form. The organic solvent requires high safety precautions. In addition, the organic solvent, preferably miscible with water, necessitates large economic expenses in order to separate the organic solvent from the water after the reaction and in order to dispose of the organic solvent. Finally, according to EP-A-0 988 853, only tetraalkoxysilanes may be used, while halogen-substituted silanes, for example, are explicitly excluded.

Therefore, an object of the present invention is to provide coated metal oxide particles that avoid the drawbacks of the prior art. They should, in particular, be easy to incorporate in cosmetic formulations, be stable therein and have a low level of photocatalytic activity.

Another object is to provide a process that avoids the drawbacks of the prior art. In particular, no organic solvents should be used. Furthermore, the silicon dioxide precursors should not be restricted to only one class of compounds.

SUMMARY OF THE INVENTION

The present invention provides coated oxide particles, comprising a metal oxide core and a silicon dioxide coating surrounding the core, characterized in that the coated oxide particles have a low structure, defined by the absence of an endpoint during the dibutyl phthalate absorption.

BRIEF DESCRIPTION OF THE DRAWINGS

The preferred embodiments of the invention will be described in detail with reference to the following figures.

DETAILED DESCRIPTION OF PREFERRED EMBODIMENTS

The present invention provides coated oxide particles, comprising a metal oxide core and a silicon dioxide coating surrounding the core, characterized in that the coated oxide particles have a low structure, defined by the absence of an endpoint during the dibutyl phthalate absorption.

Structure means the degree of intergrowth of the particles, which may be measured by DBP absorption (dibutyl phthalate absorption). The low structure is expressed by the fact that no endpoint may be identified in the DBP absorption and means that the particles are only slightly intergrown.

Figure 1A:
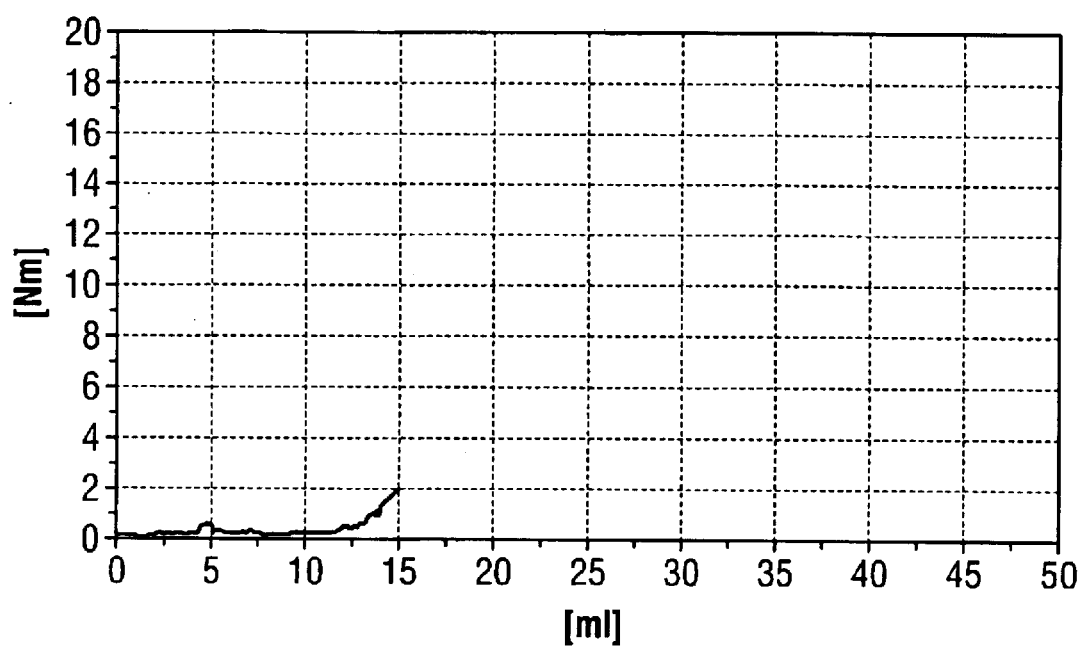
FIG. 1A shows the variation of the torque of the rotating blades of a DBP absorption (dibutyl phthalate absorption) measuring device as a function of DBP added to titanium oxide.
Figure 1B:
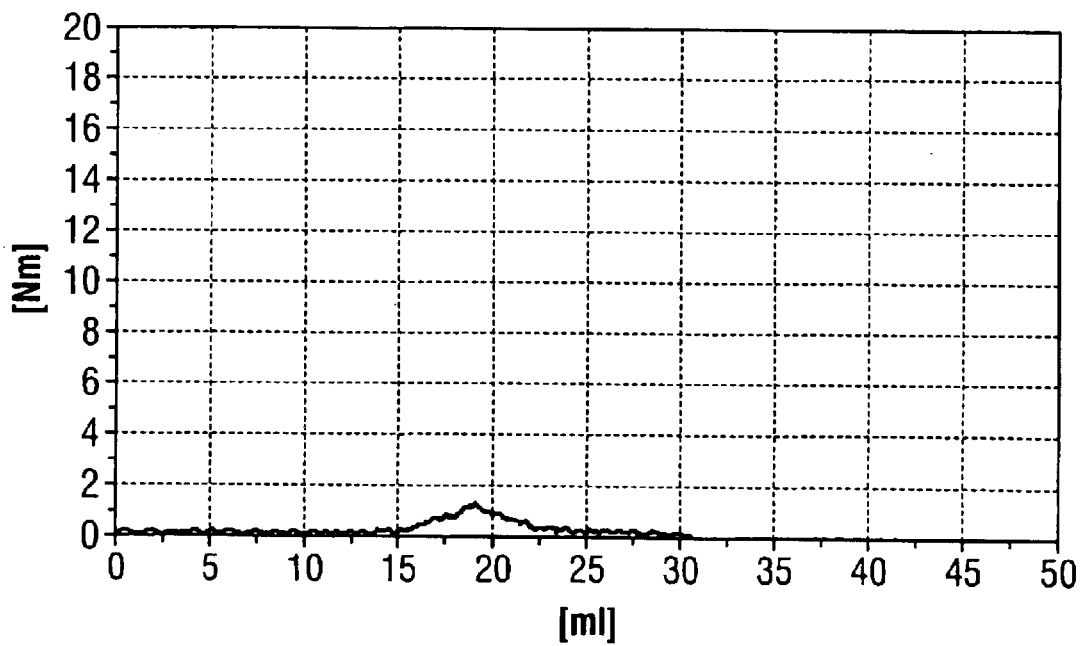
FIG. 1B shows the variation of the torque of the rotating blades of a DBP absorption measuring device as a function of DBP added to the coated oxide particles of the present invention.

The take-up of force and the measured torque (in Nm) of the rotating blades of the DBP measuring device shows a pronounced maximum with a subsequent decline at a certain addition of DBP for metal oxides, such as titanium dioxide (FIG. 1A) or silicon dioxide. With the particles according to the invention, no endpoint can be recognized (FIG. 1B).

Figure 2A:
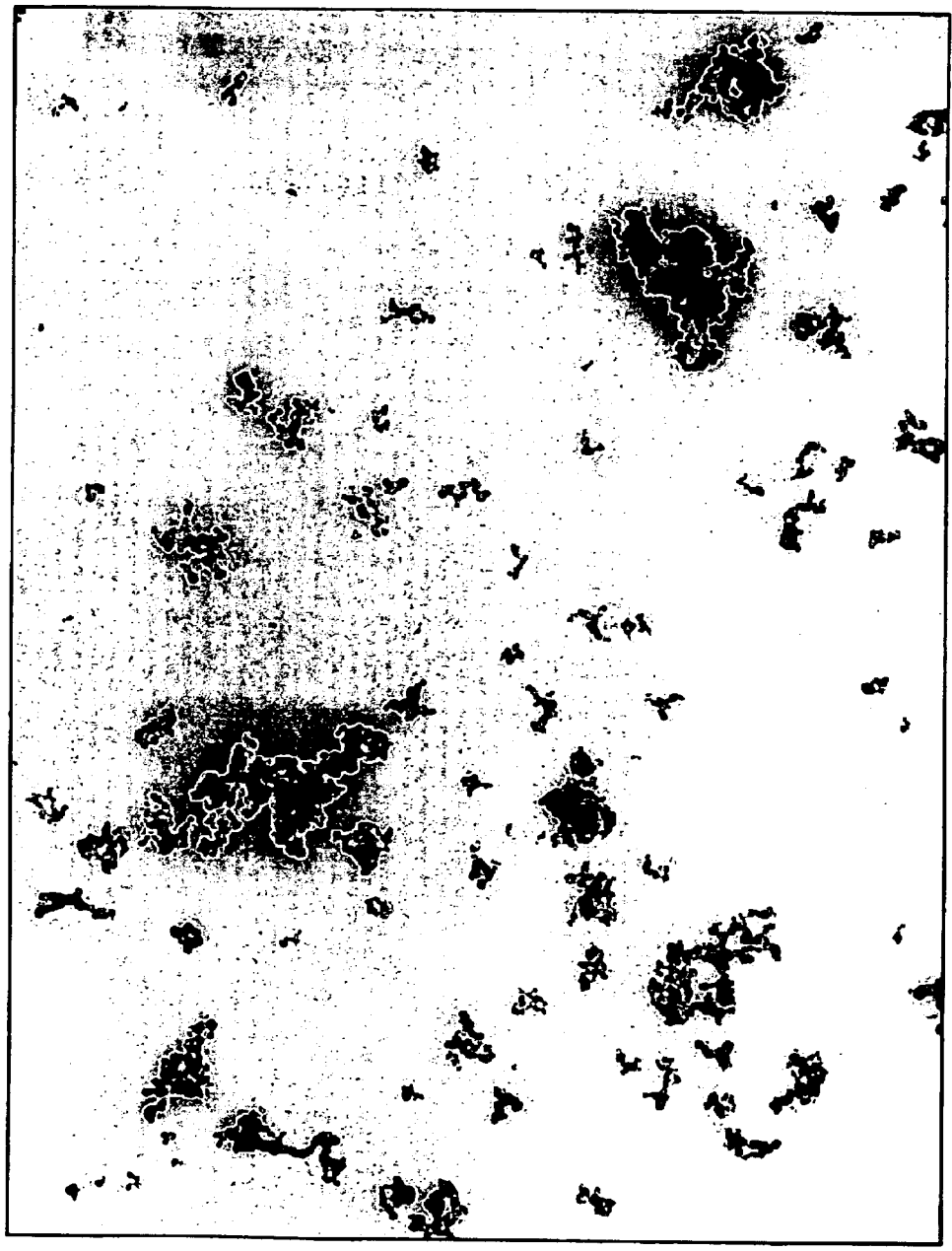
FIG. 2A is a transmission electron microscope (TEM) photograph showing the low structure of the particles of the present invention.
Figure 2B:
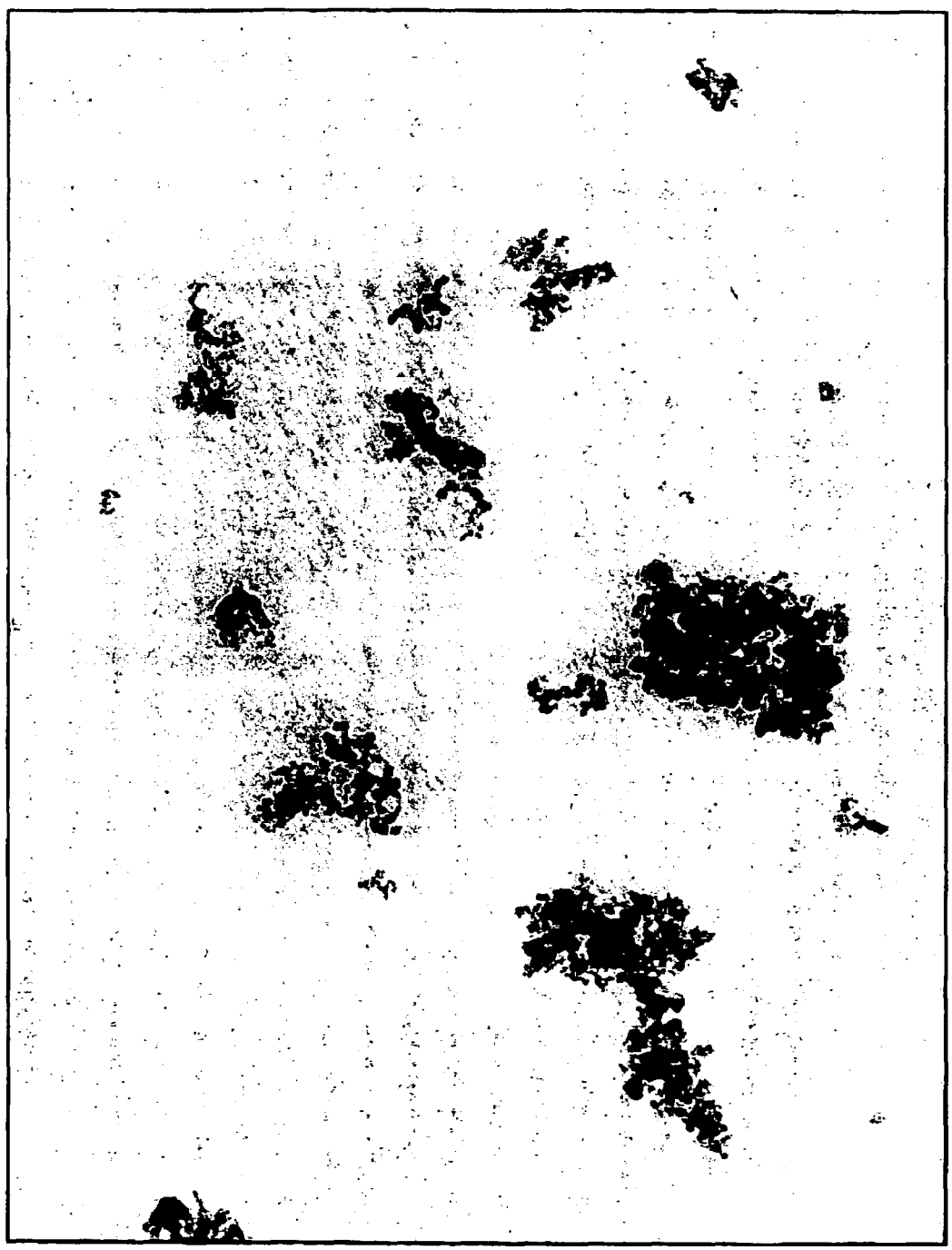
FIG. 2B is a TEM photograph showing the structure of particles produced according to EP-A-0 988 853.

The low structure of particles according to the invention may also be seen in the TEM photographs (FIG. 2A). The particles produced according to EP-A-0 988 853 show a significantly higher degree of aggregation (FIG. 2B).

The particles according to the invention preferably have a photocatalytic activity of less than $0.20 \times 10^{-3}$ mol kg$^{-1}$·min$^{-1}$. The activity is determined by the oxidation of 2-propanol to form acetone by irradiation with UV light. The result is given as the rate of formation of acetone in the form of a rate constant. The measurement is based on the method disclosed by Robert Rudham in "The Chemistry of Physical Sunscreen Materials" (Review derived from a presentation made at the FDA Workshop on the Photochemistry and Photobiology of Sunscreens, Washington, Sep. 19–20, 1996). Due to this low photocatalytic activity, the oxide particles in accordance with the invention may ideally be used in sun screening agents.

The BET surface, determined according to DIN 66131, of the particles according to the invention may be varied in a wide range between 5 and 600 m$^2$/g. Normally, the BET surface of the particles according to the invention is larger than that of the basic cores. In the case of changed production conditions, however, it may also be smaller than that of the cores used. However, preferably the BET surface of the particles according to the invention is larger than that of the basic cores.

The primary particle size of the coated oxide particles may be between 2 and 100 nm, preferably between 5 and 50 nm, and the secondary particle size may be between 0.05 and 50 µm, preferably between 0.1 and 1 µm. In these ranges, when used in sun screening agents, the particles according to the invention have satisfactory UV protection and a pleasant feeling on the skin after application.

The determination of these particle sizes is performed according to DIN 53206.

The thickness of silicon dioxide coating of the metal oxide particles according to the invention may be varied between 0.5 and 25 nm. In this range, the particles have sufficiently high UV absorption, reflection and scattering.

Metal oxides may be titanium dioxide, zinc oxide, zirconium oxide, iron oxide, cerium oxide and/or chemical mixtures of these metal oxides with each other and/or chemical mixtures of these metal oxides with aluminium oxide and/or chemical mixtures of these metal oxides with silicon dioxide. The origin of the metal oxides is not restricted. For example, metal oxides originating from a pyrogenic process, a sol-gel process, a plasma process, a precipitation process, a hydrothermal process or from mining processes or from combinations of the above-named processes may be used.

Particularly preferred metal oxides are the pyrogenic metal oxides titanium dioxide, zinc oxide, iron oxide, cerium oxide, zirconium oxide and/or chemical mixtures of these metal oxides with each other and/or chemical mixtures of these metal oxides with aluminium oxide and/or chemical mixtures of these metal oxides with silicon dioxide.

Chemical mixtures of pyrogenic oxides should, for example, be understood to mean those in which one component is incorporated in the pyrogenic process via an aerosol, as described in EP-B-0 850 876. It is also possible for both components to be vaporised simultaneously and fed into the mixing chamber of a burner as used for the production of pyrogenic oxides. Examples are given in EP-A-609 533 for titanium-silicon mixed oxide and titanium-aluminium mixed oxide or in EP-A-1 048 617 for silicon-aluminium mixed oxide. It is also possible for a pyrogenic metal oxide to be coated or partially coated with another metal oxide, which is applied to the pyrogenic metal oxide in a non-pyrogenic process.

The invention also provides a process for the production of the oxide particles in accordance with the invention. For this, a base dissolved in water is added under agitation to a dispersion comprising 1–80 wt. % of a metal oxide, at least one compound of the type $X_nSi(OR)_{4-n}$, with the molar ratio $X_nSi(OR)_{4-n}$/metal oxide, depending upon the thickness of the silicon dioxide coating, being between 0.1 and 25, and water, the reaction product is separated and optionally washed and dried.

The separation of the reaction product may be performed by filtration or centrifugation. The washing may be performed with water, an organic solvent or mixtures of water with organic solvents, with water being preferred for the purposes of the invention.

The particles according to the invention may be dried using the methods known to the person skilled in the art. An overview of various drying procedures is given in Ullmann's Encyclopedia of Industrial Chemistry, Vol. B2, Unit Operations 1, pages 4–2 to 4–35, $5^{th}$ edition.

Other process steps can follow, like calcination, grinding procedures, granulation procedures, or dispersion in suitable liquid media.

The temperature at which the reaction is performed is not critical as long as the reaction medium is liquid. A reaction temperature of from 15 to 30° C. is preferred.

The quantity of base required may be varied over a wide range from 0.1 to 30 wt. % relative to the total reaction medium. It has been found that a base concentration of from 1 to 5 wt. % is particularly advantageous, as with a low base usage there is a rapid formation of the oxide particles in accordance with the invention.

The base used may be ammonia; hydroxides such as sodium hydroxide, potassium hydroxide or tetraalkylammonium hydroxide; carbonates such as ammonium carbonate, ammonium hydrogen carbonate, sodium carbonate or sodium hydrogen carbonate; organic bases such as amines, pyridines, anilines, or guanidine; ammonium salts of carboxylic acids such as ammonium formate, or ammonium acetate; alkylammonium salts of carboxylic acids such as monomethylamine formate, or dimethylamine formate; and mixtures thereof.

Particularly preferable are ammonia, ammonium carbonate, ammonium hydrogen carbonate, ammonium formate, ammonium acetate, sodium carbonate and sodium hydrogen carbonate and mixtures of two or more compounds thereof. In addition to bases, inorganic acids, such as for example hydrochloric acid, sulphuric acid or phosphoric acid, and organic acids, such as formic or acetic acid, may be used to liberate silicon dioxide from the silicon dioxide source.

Metal oxides may be titanium dioxide, zinc oxide, zirconium oxide, iron oxide, cerium oxide, and/or chemical mixtures of these metal oxides with each other and/or chemical mixtures of these metal oxides with aluminium oxide and/or chemical mixtures of these metal oxides with silicon dioxide. The origin of the metal oxides is not restricted. For example, metal oxides originating from a pyrogenic process, a sol-gel process, a plasma process, a precipitation process, a hydrothermal process or from mining processes or from combinations of the aforesaid processes may be used.

Particularly preferred metal oxides are the pyrogenic metal oxides titanium dioxide, zinc oxide, iron oxide, cerium oxide, zirconium oxide and/or chemical mixtures of these metal oxides with each other and/or chemical mixtures of these metal oxides with aluminium oxide and/or chemical mixtures of these metal oxides with silicon dioxide, with at least one metal oxide being of pyrogenic origin.

As compounds of the type $X_nSi(OR)_{4-1}$, preferably used are those in which X=halogen or H, R=H or a linear or a branched alkyl group with 1 to 8 C atoms and n=0–4 where R unequal to H for n=4 is possible. Particularly preferable are tetraalkoxysilanes and/or their oligomers.

The advantage of the process according to the invention is that no organic solvent is used. Unlike the process described in EP-A-0 988 853, in which an organic solvent is essential for the formation of the coating, in the process according to the present invention, particles with a complete coating are obtained in a rapid reaction. It has also been demonstrated that the particles obtained in this way are uniform, i.e. only the particles according to the invention were identified. Particles consisting exclusively of silicon dioxide formed by the intergrowth of the silicon dioxide source formed by the fine $SiO_2$ particles during the hydrolysis of the silicon dioxide source could not be identified. Evidently, the metal oxides used in accordance with the invention have a high affinity with the silicon dioxide source.

The particles according to the invention have a low structure and are therefore easy to incorporate in cosmetic formulations which are resistant to sedimentation.

The invention also provides sun screening agents containing the oxide particles in accordance with the invention in a proportion of 0.01 and 25 wt. %. In addition, the sun screening agent according to the invention may be used in mixtures with known inorganic UV-absorbing pigments and/or chemical UV filters.

UV absorbing pigments that can be used are titanium dioxides, zinc oxides, aluminium oxides, iron oxides, silicon dioxide, silicates, cerium oxides, zirconium oxides barium sulphate or mixtures thereof.

Chemical UV filters that can be used are all water- or oil-soluble UVA- and UV-B filters known to the person skilled in the art, of which the following are mentioned as examples but not restrictively, sulphonic acid derivatives of benzophenones and benzimidazole derivatives of dibenzoylmethane, benzylidene camphor and their derivatives, derivatives of cinnamic acid and their esters, or esters of salicylic acid.

The sun screening agents according to the invention may also contain the solvents known to the person skilled in the art such as water, mono- or polyhydric alcohols, cosmetic oils, emulsifiers, stabilisers, consistency regulators such as carbomers, cellulose derivatives, xanthane gum, waxes, bentones, pyrogenic silicic acids and other usual substances used in cosmetics such as vitamins, antioxidants, preservatives, colorants and perfumes.

Typically, the sun screening agents according to the invention may be present as emulsions (O/W, W/O or multiple), aqueous or aqueous-alcohol gel or oil gel and in the form of lotions, creams, milk sprays, mousses, as sticks or in other common forms.

The general structure of sun screening agents is also described in A. Domsch, "Cosmetic Preparations", Verlag für chemische Industrie (ed. H. Ziolkowsky), 4$^{th}$ edition, 1992 or N. J. Lowe and N. A. Shaat, Sunscreens, Development, Evaluation and Regulatory Aspects, Marcel Dekker Inc., 1990.

The invention also provides the use of oxide particles in accordance with the invention as UV filters, for the production of dispersions and use for chemical-mechanical polishing (CMP process).

EXAMPLES

Examples 1–6 are performed in accordance with the process according to the invention. The comparative examples 1–3 are performed in the presence of an organic solvent, ethanol. All examples include the drying of the product after filtration at room temperature. A 29 wt. % aqueous ammonia solution is used as the base.

The analytical data may be found in the table following the examples.

The composition of the core and coating is determined by quantitative X-ray fluorescence analysis, the thickness of the coating from the TEM photographs. The BET surface is determined according to DIN 66131 and the particle pore volume according to DIN 66134. The hydroxyl group density is determined according to the method disclosed by J. Mathias and G. Wannemacher in the Journal of Colloid and Interface Science 125 (1998).

The dibutyl phthalate absorption is measured with a RHEOCORD 90 made by Haake, Karlsruhe. For this, 16 g of the described metal oxides are fed into a kneading chamber with an accuracy of 0.001 g, this is then sealed with a lid and dibutyl phthalate added through a hole in the lid at a prespecified feed rate of 0.0667 ml/s. The kneader is operated at a motor speed of 125 revolutions a minute. When the maximum torque is attained, the kneader and the DBP feed is automatically switched off. The DBP absorption is calculated from the quantity of DBP consumed and the weighed quantity of particles as follows: DBP count (ml/100 g)=(consumption of DBP in ml/weighed portion of particles in g)×100. FIGS. 1A and 1B refer to DBP in millilitres (ml) as x-axis and torque in Newton meter (Nm) as y-axis.

FIG. 1A shows the typical behaviour of pyrogenic oxides with a clearly pronounced maximum and subsequent drop on a specific addition of DBP. FIG. 1B shows the behaviour of the particles according to the invention. Here, an increase in torque with a subsequent drop with a specific addition of DBP is not identified. The DBP device does not detect any endpoint.

FIG. 2A shows a TEM photograph of the particles according to the invention according to example 1. FIG. 2B shows in the same magnification a TEM photograph of the particles, produced according to comparative example 1. FIG. 2A shows the significantly lower degree of intergrowth of the particles according to the invention.

For the determination of photocatalytic activity, the sample to be measured is suspended in 2-propanol and irradiated for 1 h with UV light. After that, the concentration of acetone formed is measured.

Approximately 250 mg (accuracy 0.1 mg) of the particles obtained from the examples and comparative examples are suspended with an Ultra-Turrax mixer in 350 ml (275.1 g) of 2-propanol. This suspension is conveyed by means of a pump through a cooler set to a temperature of 24° C. into a glass photoreactor which has previously with rinsed with oxygen with a radiation source.

The radiation source is, for example, a Hg-medium-pressure immersion lamp of the type TQ718 (Heraeus) with a power of 500 Watts. A protective tube made of boron silicate glass limits the radiation emitted to wavelengths of >300 mn. The radiation source is surrounded on the outside by a cooling tube conveying water.

Oxygen is fed into the reactor through a flowmeter. When the radiation source is switched on, the reaction starts. At the end of the reaction, a small amount of the suspension is immediately removed, filtered and analysed by means of gas chromatography.

Example 1

100 g of pyrogenic titanium dioxide (P25 from Degussa) are dispersed in 1 l of water. 100 ml of tetraethoxysilane are added to this solution. This mixture is agitated for 15 min and then 30 ml of ammonia are added. After 2–4 hours of agitation at 25° C., the product is filtered off and dried.

Example 2

100 g of pyrogenic titanium dioxide (P25 from Degussa) are dispersed in 1 l of water. 200 ml of tetraethoxysilane are added to this solution. This mixture is agitated for 15 min and then 30 ml of ammonia are added. After 2–4 hours of agitation at 25° C., the product is filtered off and dried.

Example 3

100 g of pyrogenic titanium dioxide (P25 from Degussa) are dispersed in 1 l of water. 100 ml of tetramethoxysilane are added to this solution. This mixture is agitated for 15 min and then 30 ml of ammonia are added. After 2–4 hours of agitation at 25° C., the product is filtered off and dried.

Example 4

100 g of pyrogenic titanium dioxide (P25 from Degussa) are dispersed in 1 l of water. 1000 ml of tetraethoxysilane are added to this solution. This mixture is agitated for 15 min and then 30 ml of ammonia are added. After 2–4 hours of agitation at 25° C., the product is filtered off and dried.

Example 5

100 g of a pyrogenic titanium dioxide with a BET surface of 100 m$^2$/g are dispersed in 1 l of water. 200 ml of tetraethoxysilane are added to this solution. This mixture is agitated for 15 minutes and then 30 ml of ammonia are added. After 2–4 hours of agitation at 25° C., the product is filtered off and dried.

Example 6

100 g of pyrogenic titanium dioxide doped with 0.2% of Al$_2$O$_3$, (produced in accordance with DE-A-196 50 500) are dispersed in 1 l of water. 200 ml of tetraethoxysilane are added to this solution. This mixture is agitated for 15 minutes and then 30 ml of ammonia are added. After 2–4 hours of agitation at 25° C., the product is filtered off and dried.

Comparative Example 1

100 g of pyrogenic titanium dioxide (P25 from Degussa) are dispersed in 1.5 l of ethanol and 100 ml water. 50 ml ammonia are added to this solution. Then, 100 ml of tetraethoxysilane in 200 ml ethanol are added in drops to this mixture slowly over a period of 1 h. After 12 h, the product is filtered off and dried.

Comparative Example 2

400 ml water, 1388 ml of ethanol and 87 ml ammonia are mixed, then, 105 g of titanium dioxide are dispersed therein. 193 ml of tetraethoxysilane in 24 ml water and 156 ml of ethanol are added to this solution over a period of 6 h. The dispersion is aged for another 12 h at 25° C. The product is filtered off and dried.

Comparative Example 3

106 ml water, 480 ml Ethanol and 20 ml ammonia are mixed, then, 28 g titanium dioxide are dispersed therein. 105 ml of tetraethoxysilane in 39.5 ml water and 65.5 ml of ethanol are added to this solution over a period of 2 h. The dispersion is aged for another 12 h at 20° C. The product is then recovered by filtration and dried.

rpm and under a vacuum. Phase D is also heated to 70° C. and added to the mixture of A-C under vacuum.

The disclosure of the priority document, EP 01 119 108.7, filed in the European Patent Office on Aug. 8, 2001, is incorporated by reference herein in its entirety.

What is claimed is:

1. A coated oxide particle comprising,
   a core comprising a metal oxide, and
   a coating comprising silicon dioxide surrounding the core, wherein
      the coated oxide particle has a low degree of aggregation defined by the absence of an endpoint during dibutyl phthalate absorption.

2. The coated oxide particle according to claim 1, wherein the photocatalytic activity of the coated oxide particle determined by the oxidation of 2-propanol to form acetone, is less than $0.20 \times 10^{-3}$ mol kg$^{-1}$ min$^{-1}$.

3. The coated oxide particle according to claim 1, wherein the coating has a thickness of from 0.5 to 25 nm.

4. The coated oxide particle according to claim 1, wherein the metal oxide comprises at least one selected from the

TABLE

| | Core[1] (wt. %) | Coating[2] (wt. %) | Coating (nm) | DBP absorption (ml/100 g) | k ($10^{-3}$ mol kg$^{-1}$ min$^{-1}$) | BET surface (m$^2$/g) | OH density (OH/nm$^2$) | Pore volume (cm$^3$/g) |
|---|---|---|---|---|---|---|---|---|
| Example | | | | | | | | |
| P25[3] | 99.5 | — | — | 96 | 0.68 | 50 | 23.2 | — |
| 1 | 88.1 | 11.7 | 2 | no endpoint | 0.08 | 64 | 8.1 | 0.12 |
| 2 | 80.0 | 20 | 3–4 | no endpoint | 0.10 | 80 | 4.4 | 0.16 |
| 3 | 85.7 | 14.3 | 3 | no endpoint | 0.14 | 75 | 5.2 | 0.14 |
| 4 | 37.7 | 62.3 | 16–18 | no endpoint | 0.09 | 63 | 4.9 | 0.15 |
| 5[4] | 63.7 | 36.2 | 7 | no endpoint | 0.12 | 123 | 5.3 | 0.21 |
| 6[5] | 80.1 | 18.7 | 3–4 | no endpoint | 0.16 | 77 | 6.2 | 0.15 |
| Comparative example | | | | | | | | |
| 1 | 80.2 | 19.8 | 3 | ND | 0.28 | 40 | — | 0.08 |
| 2 | 68.1 | 31.9 | 10 | ND | 0.42 | 40 | 2.2 | 0.07 |
| 3 | ND[6] | ND | 3 | ND | 0.38 | 35 | ND | 0.06 |

[1]Core: examples 1 to 4, all comparative examples: TiO$_2$ with approx. 50 m$^2$/g BET;
[2]Coating examples 1, 2, 4–6, all comparative examples: SiO$_2$ source: Si(OEt)$_4$, example 3: Si(OMe)$_4$
[3]P25: Pyrogenic titanium dioxide, Degussa
[4]TiO$_2$ with approx. 100 m$^2$/g
[5]TiO$_2$ doped with 0.1 wt. % Al$_2$O$_3$ with approx. 50 m$^2$/g BET
[6]ND = no data Sun Screening Agents The following formulation was used to produce a sun screening agent with 4 wt. % of the particles according to the invention in accordance with example 2.

| Phase | Component | wt. % |
|---|---|---|
| A | Isolan GI 34 | 3.0 |
| | Castor oil | 1.2 |
| | Tegesoft OP | 10.0 |
| | Tegesoft Liquid | 5.0 |
| | Glycerol 86% | 3.0 |
| B | Paracera W80 | 1.8 |
| | Isohexadecane | 5.0 |
| C | Particles according to the invention in accordance with example 2 | 4.0 |
| D | Magnesium sulphate | 0.5 |
| | Deionised water | 66.5 |

Phase A is heated in a mixer to 70° C. After melting on a magnetic hot plate at 80° C. phase B is added to phase A. Phase C is stirred into the oil phase at approximately 300 group consisting of titanium dioxide, zinc oxide, zirconium oxide, iron oxide, and cerium oxide.

5. The coated oxide particle according to claim 4, wherein the metal oxide further comprises at least one selected from the group consisting of aluminum oxide and silicon dioxide.

6. The coated oxide particle according to claim 1, wherein the metal oxide comprises at least one selected from the group consisting of pyrogenic titanium dioxide, pyrogenic zinc oxide, pyrogenic zirconium oxide, pyrogenic iron oxide, and pyrogenic cerium oxide.

7. The coated oxide particle according to claim 6, wherein the metal oxide further comprises at least one selected from the group consisting of aluminum oxide and silicon dioxide.

8. A process for producing a coated oxide particle comprising,
   forming a reaction mixture by adding under agitation a base dissolved in water to a dispersion comprising
      1 to 80 wt. % of a metal oxide,
      at least one compound of the formula X$_n$Si(OR)$_{4-n}$, where X is a halogen or H, R is H or a linear or branched alkyl group with 1 to 8 C atoms and n is 0 to 4, with the molar ratio X$_n$Si(OR)$_{4-n}$/metal oxide being from 0.1 to 25, and water; wherein the reaction mixture does not contain or organic solvent;

separating a reaction product from the reaction mixture;

optionally washing the reaction product;

drying the reaction product; and producing the coated oxide particle of claim 1.

9. The process according to claim 8, wherein the metal oxide comprises at least one selected from the group consisting of titanium dioxide, zinc oxide, zirconium oxide, iron oxide, and cerium oxide.

10. The process according to claim 9, wherein the metal oxide further comprises at least one selected from the group consisting of aluminum oxide and silicon dioxide.

11. The process according to claim 8, wherein the metal oxide comprises at least one selected from the group consisting of pyrogenic titanium dioxide, pyrogenic zinc oxide, pyrogenic zirconium oxide, pyrogenic iron oxide, and pyrogenic cerium oxide.

12. The process according to claim 11, wherein the metal oxide further comprises at least one selected from the group consisting of aluminum oxide and silicon dioxide.

13. The process according to claim 8, wherein X is the halogen.

14. The process according to claim 13, wherein R is the a linear or branched alkyl group with 1 to 8 C atoms and n is 4.

15. A sun screening agent containing coated oxide particles of claim 1 in a proportion of from 0.01 to 25 wt. % relative to the quantity of the sun screening agent.

16. A method of using coated oxide particles comprising, dispersing the coated oxide particles of claim 1 in a cosmetic composition to form a sun screening agent.

17. A method of using coated oxide particles comprising, filtering UV radiation with the coated oxide particles of claim 1.

18. A method of using coated oxide particles comprising, chemical-mechanical polishing a material with the coated oxide particles of claim 1.

19. Coated oxide particles comprising, a core comprising a metal oxide, and a coating comprising silicon dioxide surrounding the core, wherein the coated oxide particles have a low degree of aggregation defined by the absence of an endpoint during dibutyl phthalate absorption, and wherein a BET surface is from 5 to 600 $m^2/g$.

20. Coated oxide particles comprising, a core comprising a metal oxide, and a coating comprising silicon dioxide surrounding the core, wherein the coated oxide particles have a low degree of aggregation defined by the absence of an endpoint during dibutyl phthalate absorption, and wherein a primary particle size is from 2 to 100 nm and a secondary particle size is from 0.05 to 50 $\mu$m.

* * * * *